United States Patent [19]

Heidt et al.

[11] Patent Number: 5,667,901
[45] Date of Patent: Sep. 16, 1997

[54] CROSSLINKERS BASED ON 2-ACETYLGLUTARATE ESTERS OF POLYOLS

[75] Inventors: Philip C. Heidt; Charles H. Foster, both of Kingsport, Tenn.; J. Stewart Witzeman, Den Haag, Netherlands

[73] Assignee: Eastman Chemical Company, Kingsport, Tenn.

[21] Appl. No.: 603,489

[22] Filed: Feb. 20, 1996

Related U.S. Application Data

[63] Continuation of Ser. No. 468,456, Jun. 6, 1995, abandoned, which is a continuation of Ser. No. 139,662, Oct. 22, 1993, abandoned.

[51] Int. Cl.$^6$ ........................... B32B 27/06
[52] U.S. Cl. ........................... 428/482; 428/522; 525/386; 525/437; 525/450; 560/146; 560/176
[58] Field of Search ............... 525/386, 437, 525/450; 560/54, 146, 176; 428/482, 522

[56] References Cited

U.S. PATENT DOCUMENTS

| | | | |
|---|---|---|---|
| 2,730,517 | 1/1956 | Vogel et al. | 260/75 |
| 3,892,903 | 7/1975 | Dowbenko | 428/460 |
| 4,408,018 | 10/1983 | Bartman et al. | 525/300 |
| 4,795,787 | 1/1989 | Walz | 525/328.2 |
| 5,107,649 | 4/1992 | Benson et al. | 52/309.4 |
| 5,219,958 | 6/1993 | Noomen et al. | 525/10 |
| 5,247,122 | 9/1993 | Witzeman et al. | 560/51 |
| 5,359,125 | 10/1994 | Witzeman et al. | 560/54 |
| 5,412,151 | 5/1995 | Heidt et al. | 560/145 |
| 5,453,464 | 9/1995 | Witzeman et al. | 525/153 |
| 5,466,863 | 11/1995 | Heidt et al. | 560/176 |

FOREIGN PATENT DOCUMENTS 07-048472  2/1995  Japan.

OTHER PUBLICATIONS

R. J. Clemens and F. D. Rector, Journal of Coatings Technology, vol. 61, No. 770, 83, (1989).

*Primary Examiner*—Mark D. Sweet
*Attorney, Agent, or Firm*—Bernard J. Graves, Jr.; Rose M. Allen; Harry J. Gwinnell

[57] ABSTRACT

Provided are various 2-acetylglutarate esters of polyols which are useful as poller crosslinkers for use in thermosetting coating compositions, as well as methods of preparation of these materials. In particular, the invention provides crosslinkers of the formula

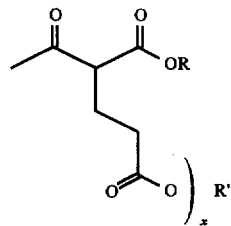

wherein R and R' are independently t-butyl, t-amyl, or phenyl, and x is an integer of from 2 to 5.

10 Claims, No Drawings

CROSSLINKERS BASED ON 2-ACETYLGLUTARATE ESTERS OF POLYOLS

This is a continuation of application Ser. No. 08/468,456 filed on Jun. 6, 1995, now abandoned which is a continuation of Ser. No. 08/139,662, filed on Oct. 22, 1993 now abandoned.

FIELD OF THE INVENTION

This invention relates to the field of organic chemistry. More particularly, this invention relates to 2-acetylglutarate esters of polyols as polymer crosslinkers for use in thermosetting coating compositions, as well as methods of preparation of these materials.

BACKGROUND OF THE INVENTION

Crosslinkers are multi-functional molecules capable of reacting with pendant functional groups on polymers. The use of crosslinkers enables one to increase the molecular weight of the resin or polymer and thus improve the properties of the resulting polymer or polymeric film. Most crosslinking reactions are initiated by heating a mixture of the polymer and the crosslinker either neat or in a solvent. Such systems are often referred to as "thermosetting" systems.

Crosslinkers are particularly useful in coating applications due to the fact that the crosslinker enables the use of relatively low molecular weight polymers and resins which are easily handled and applied in solvents. The formulation can subsequently be applied to the substrate and heated, or cured, to give the finished (thermoset) coating. This feature makes it possible to take advantage of the ease of handling and solubility characteristics of the lower molecular weight resins used in the formulation and subsequently develop the hardness, chemical and solvent resistance, as well as strength properties desired in the ultimate coating by the reaction of the crosslinker with the resin during the curing process.

Crosslinkers are becoming increasingly important due to the emphasis on more environmentally acceptable coatings. One major environmental concern in the coatings industry is the amount of organic solvent released during the curing process. This solvent level or Volatile Organic Content (VOC) is of concern due to the role of organic solvents in the development of photochemical smog. For these reasons various governments, including the U.S., are regulating the VOC levels of coating formulations. One way to reduce the amount of solvent necessary in a coating formulation is to reduce the molecular weight of the resin backbone used in the formulation. When this approach is used, however, crosslinking becomes even more critical to the development of the ultimate properties in the cured film.

Properties of Crosslinked Films and Coatings

A number of properties are desired in a coating in order to impart the desired protection of the object from corrosion and other environmental factors. Some of the protective characteristics that are ultimately desired include the resistance of the coating to various chemicals and solvents, the impact strength of the system, the hardness of the coating and the weatherability or resistance of the system to various factors related to environmental exposure.

I) Chemical and Solvent Resistance

In order for a coating to impart adequate protection to the object coated it must be resistant to various chemicals and solvents. If a coating is not resistant to solvents and chemicals the coating could be removed or the protective integrity compromised by exposure to commonly used materials such as industrial cleaners, gasoline, etc. A commonly used test to assay this property is the methyl ethyl ketone (MEK) rub resistance of the coating. The MEK rub resistance of a coating is often one of the most useful diagnostic tests for crosslinking in coatings. For most applications, a MEK rub resistance of greater than 175–200 is desired.

II) Impact Strength

In order for a coating to be resistant to collisions and other sudden impacts the material must have certain strength characteristics. If a coating does not possess enough strength, a physical impact with another object will lead to chipping and breaking of the coating which, in turn, compromises the protective integrity of the film. A commonly used test for the impact strength of a coating (ASTM D2794-84) is performed by dropping a weight from various heights on a coated panel and determining the foot-lbs. of force required to break the coating. Proper crosslinking can help develop the impact strength of a coating.

III) Hardness

In order for a coating to be resistant to scratching and other such abrasions the coating must possess a certain degree of hardness. This resistance to scratching is often determined by marring the coating with pencils of various hardness and noting which hardness of pencil actually scratches the coating.

Hardness and impact strength often work in opposite directions. This is due to the fact that impact strength reflects both the strength and the flexibility of the polymeric film, while hardness reflects primarily just the strength, or rigidity of the film. Thus, one often seeks a combination of hardness and flexibility by compensating one of the above characteristics for the other.

The compensation of these two factors is best understood by invoking the theory of crosslink density (see, for example, Vogel, H. A. and Bader, A. R., U.S. Pat. No. 2,730,517). If the coating formulation consists of a group of polyfunctional (n>2) polymer molecules and crosslinker then the crosslinking process can be thought of as consisting of a series of steps. Initially, the crosslinking reaction consists of intermolecular reactions of various polymer chains. During this initial phase the chains are combining and thus building in molecular weight, but, the mobility of the polymer chains is not greatly restricted. This stage would be characterized by improvement in the chemical resistance, hardness and impact strength of the film. At some point, however, intermolecular reaction is essentially complete and intramolecular reaction becomes significant. At this point, the polymer becomes more rigid due to restriction of the polymer chain mobility by these intramolecular reactions and the resulting coating becomes more brittle. At this stage, hardness will improve but the impact strength will decrease due to the increased rigidity of the polymer network. The balance between flexibility and hardness can be controlled by the amount of crosslinker used, the average functionality of the polymer and crosslinker as well as the chemical structure of the polymer or crosslinker.

IV) Resistance to Atmospheric Exposure (Weathering)

Since many coated objects are exposed to severe weather conditions, the performance of the coating under various exposure conditions is very important. Factors which affect the weatherability of the coating include the composition of the polymer and the crosslinker, as well as the degree of crosslinking. A variety of exposure tests are available which enable one to determine the performance of the system to severe conditions.

3

Crosslinkers Currently Used in the Field

A large number of crosslinkers are used in various applications. A partial list of the more commonly types of compounds used as crosslinkers include:

Polyepoxides

Polyisocyanates

Amino resins (e.g. melamines)

Polyunsaturated compounds

These materials take advantage of the reaction of the aforementioned functional groups with various pendant groups on the polymeric backbone. These crosslinkers can be used in combination with other crosslinkers to impart a variety of desired characteristics to the coatings. The use and reactions of these crosslinkers have been reviewed elsewhere (see U.S. Pat. No. 2,730,517, incorporated herein by reference). All of these materials are structurally very different from the 2-acetyl glutarate esters of polyols disclosed in this invention. Bisacetoacetates of general formula 1 have been shown to act as a crosslinker and are the subject of U.S. Pat. No. 5,247,122.

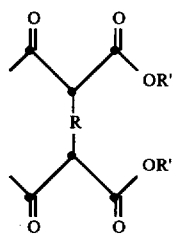
(1)

It has also been shown that acetoacetylated polymers have undergone Michael reactions with acrylates and polyacrylates to form crosslinked coatings under various conditions (usually strongly basic). (See, for example, Clemens, R. J. and Rector, F. D.; Journal of Coatings Technology, Vol. 61, No 770, 83, (1989); Vogel, H. A. and Bader, A. R., U.S. Pat. No. 2,730,517; Bartman, B. and Swift, G., U.S. Pat. No. 4,408,018); Noomen, A., van Dongen, J. P. M., and Klinkenberg, H., European Patent Application 91200528.7; and U.S. Pat. No. 5,107,649.)

Finally, U.S. Pat. No. 4,795,787 describes the Michael addition products of monocarboxylic or dicarboxylic acid esters capable of undergoing Michael addition with compounds containing at least two double bonds and are taught to be useful as crosslinkers in coating systems utilizing amine-containing or hydroxyl-containing resins.

SUMMARY OF THE INVENTION

This invention provides various 2-acetylglutarate esters of polyols which are useful as polymer crosslinkers for use in thermosetting coating compositions, as well as methods of preparation of these materials. In particular, the invention provides crosslinkers of formula (2) as shown below. Also provided is a process for preparing compounds of formula (2) via the addition of certain acetoacetates to trimethylolpropane triacrylate.

DETAILED DESCRIPTION OF THE INVENTION

The present invention provides compounds of the formula

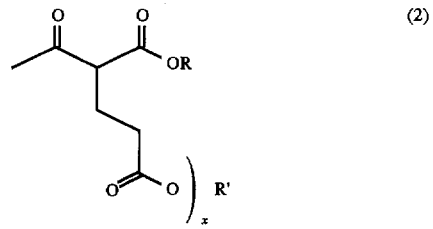
(2)

wherein R is t-butyl, t-amyl, or phenyl;

R' is a di, tri, or tetra-functional polyol residue; and x is an integer of from 2 to about 5. Examples of such polyols include trimethylolpropane, trimethylolethane, pentaerythritol, glycerine, and carbohydrates such as glucose, sucrose, and the like.

The preparation of glutarates such as compound 3, prepared by the Michael addition of three acetoacetate molecules to each trimethylolpropane triacrylate molecule as shown below.

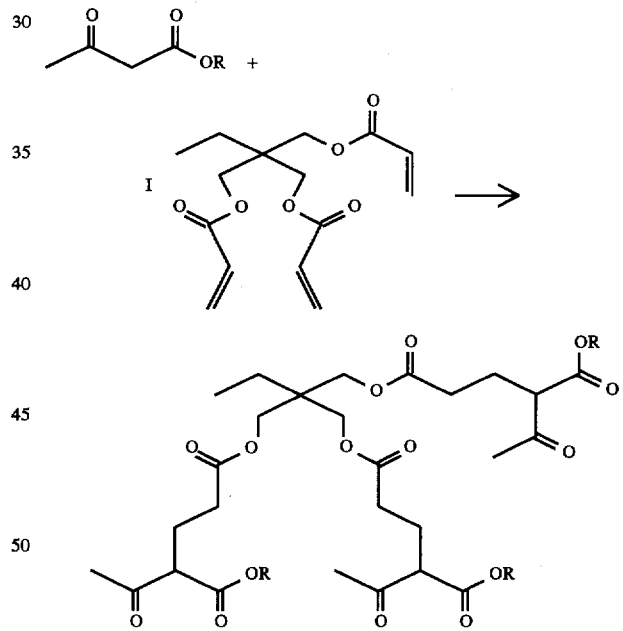

wherein R is t-butyl, t-amyl, or phenyl.

It has been shown that acetoacetates can react twice with two different acrylates (Clemens, R. J. and Rector, F. D.; Journal of Coatings Technology, Vol 61, No 770, 83, (1989)). Thus, products of the type 4 and 5 below can form (formed by intramolecular and intermolecular Michael reactions respectively). Formulations prepared using reaction products as prepared in Example 4 contain such compounds.

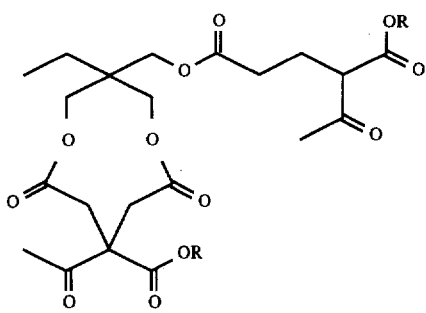

(4)

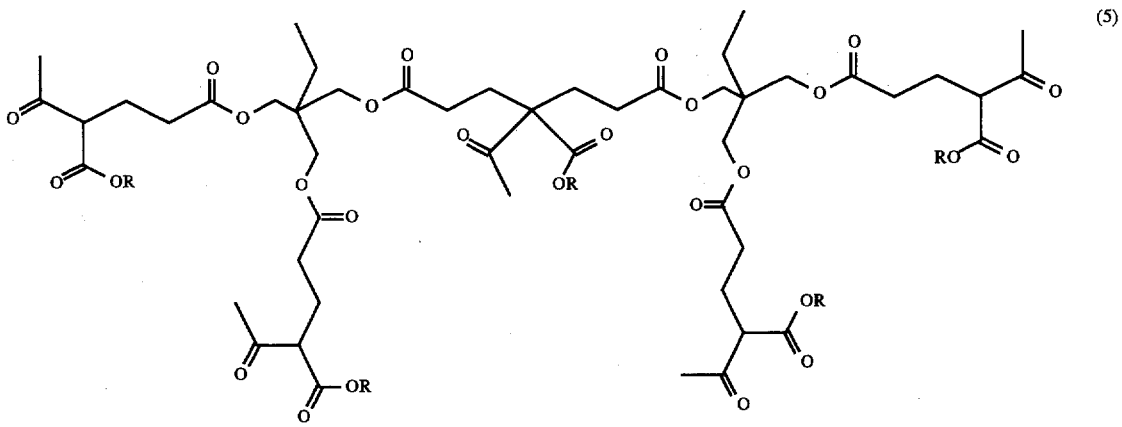

(5)

As a further aspect of the present invention, there are provided compounds of formula 3, 4, and 5.

Bases that can be used to prepare the 2-acetylglutarate esters include sodium hydroxide, potassium hydroxide, sodium methoxide, sodium hydride, potassium carbonate, sodium carbonate, potassium tert-butoxide, tetramethylguanidine, trimethylamine, triethylamine, tripropylamine, 1,5-diazabicyclo[4.3.0]non-5-ene, 1,8-diazabicyclo[5.4.0]undec-7-ene, sodium ethoxide, and the like.

As a further aspect of the present invention, there is provided a thermosetting coating composition having as crosslinker a compound of formula 2, 3, 4, or 5, above. In such compositions, the resin or binder component is preferably a curable polyester or acrylic resin. The acrylic component is a polymer or resin prepared by polymerization of a hydroxyl-bearing monomer such as hydroxyethyl methacrylate, hydroxyethyl acrylate, hydroxyhexyl acrylate, hydroxyhexyl methacrylate, hydroxypropyl acrylate, hydroxypropyl methacrylate, hydroxybutyl acrylate, hydroxybutyl methacrylate and the like optionally polymerized with other monomers such as methyl acrylate, methyl methacrylate, ethyl acrylate, ethyl methacrylate, butyl acrylate, butyl methacrylate, isobutyl acrylate, isobutyl methacrylate, ethylhexyl acrylate, ethylhexyl methacrylate, styrene, vinyl acetate, and the like. The polyester consists of a resin or polymer prepared by condensation of a slight excess of polyol with a polycarboxylic acid. Examples of polyols that can be used are ethylene glycol, propylene glycol, butanediol, pentanediol, hexanediol, 2-methylpropanediol, 1,3-propanediol, neopentylglycol, 2,2,4-trimethyl-1,3-propanediol, 3-methylpentanediol, trimethylolpropane, trimethylolethane, 1,4-cyclohexanedimethanol, 1,3-cyclohexanedimethanol, and the like. Examples of polycarboxylic acids include aromatic diacids such as terephthalic acid, isophthalic acid, and phthalic acid; aliphatic diacids such as malonic acid, succinic acid, glutaric acid, adipic acid, 1,4-cyclohexanedicarboxylic acid, 1,3-cyclohexanedicarboxylic acid, and the like. The ratio of reagents and molecular weights of the resulting acrylic or polyester are chosen so as to give polymers with an average functionality (the number of OH groups per molecule) greater than or equal to 2, preferably greater than or equal to 4.

Examples of commerically-available curable polyesters include CARGILL 5770, CARGILL 5722, and AROPLAZ 6455 (Spencer Kellogg). In general, such polyesters will have hydroxyl values of about 20 to 200 (mg KOH/g polymer).

Examples of commercially-available curable acrylic polymers include JONCRYL 800, JONCRYL 500, both available from S. C. Johnson & Co. and NEOCRYL LE-800, avialable from I.C.I., Americas Inc.

Solvents that can be used to dissolve or disperse the polymers and crosslinkers include aromatic solvents such as xylenes and toluene; ketone solvents such as methyl amyl ketone, methyl ethyl ketone, methyl isobutyl ketone, diisobutyl ketone, and the like; ester solvents such as ethyl acetate, butyl acetate, propyl acetate, and the like; alcohols such as butanol, and other solvents such as ethoxyethyl propionate (EEP). Optional other ingredients include pigments such as titanium dioxide, barytes, clay or calcium carbonate; flow aides such as silicones, fluorocarbons and cellulosics; colorants such as phthalocyanine blue, molybdate orange or carbon black; catalysts such as dibutyltin dilaurate, stearic acid, butylstannoic acid, dibutyltin oxide, zinc acetylacetonate, and 1,3-diacetoxy-1,1,3,3-tetrabutyldistannoxane; ultraviolet stabilizers such as ortho hydroxy benzophenones, substituted benzotriazoles, substituted acrylonitriles, nickel complexes of phenol, and hindered amines; and phenolic antioxidants.

The exact ratio of crosslinker to polymer or resin will depend on the molecular weight and functionality of each species. Generally, however, the following proportions of material will be used:

(a) about 15 to 80 percent, based on the weight of the total composition of polyester or acrylic.

(b) about 0 to 50 percent, based on the weight of the total composition of solvent.

(c) about 10 to 40 percent, based on the weight of the crosslinker described above.

Preferred amounts of (a) are about 30 to 70 percent; more preferred are about 45 to 55 percent.

Preferred amounts of (b) are about 0 to 40 percent; more preferred are about 0 to 35 percent.

Preferred amounts of (c) are about 10 to 38 percent; more preferred are about 10 to 35 percent.

The crosslinker system can include the 2-acetylglutarate esters of polyols described above by themselves or used in conjunction with other crosslinkers such as melamines, isocyanates, and epoxys.

Preferably, the crosslinker used in conjunction with the crosslinkers of the present invention is a melamine-type cross-linking agent, i.e., a cross-linking agent having a plurality of —N(CH$_2$OR$^3$)$_2$ functional groups, wherein R$^3$ is C$_1$–C$_4$ alkyl, preferably methyl.

In general, the cross-linking agent may be selected from compounds of the following formulae, wherein R$^3$ is independently C$_1$–C$_4$ alkyl:

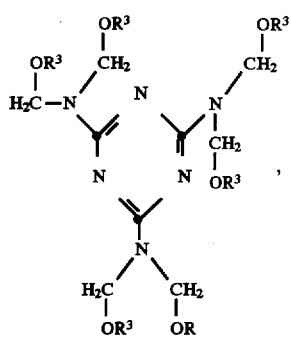

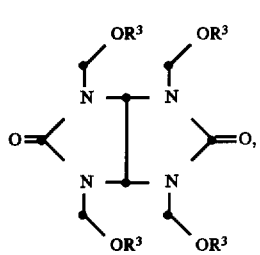

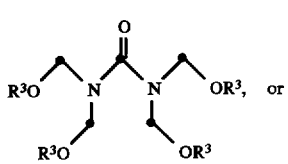

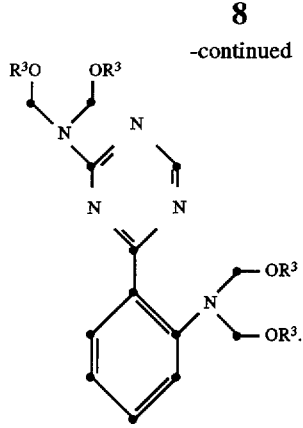

In this regard, preferred cross-linking agents include hexamethoxymethylmelamine, tetramethoxymethylbenzoguanamine, tetramethoxymethylurea, mixed butoxy/methoxy substituted melamines, and the like. The most preferred cross-linking agent is hexamethoxymethylmelamine.

The cross-linking agent may also be a isocyanate type cross-linking agent, such as tolylene diisocyanate; hexamethylene diisocyanate; isophorone diisocyanate; diphenylmethane 4,4'-diisocyanate; bis(4-isocyanato cyclohexyl) methane; Miles Labs' DESMODURS®; and blocked isocyanates. It may also be an epoxide cross-linking agent, such as compounds based on bisphenol A/epichlorohydrin; and triglycidyl isocyanurate.

As a further aspect of the present invention, there is provided a curable enamel composition further comprising one or more cross-linking catalysts. The most preferred cross-linking catalyst for melamine type cross-linking agents is p-toluenesulfonic acid.

The formulation can be applied to any object such as metal, glass, plastic and the like. The formulation is the crosslinked, or cured, by heating the material at 100°–250° C. for 1 min to 2 hours with 150°–230° C. for 5–45 min being preferred.

The exchange reaction of acetoacetates has been shown to proceed via the intermediacy of acetylketene 6(Witzeman, J. S., Tett. Lett., 31, 1401 (1990). The crosslinking process presumably involves a similar tris(acetylketene), (7).

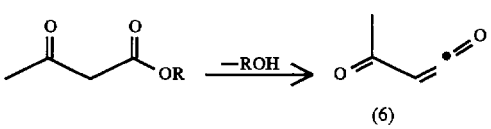

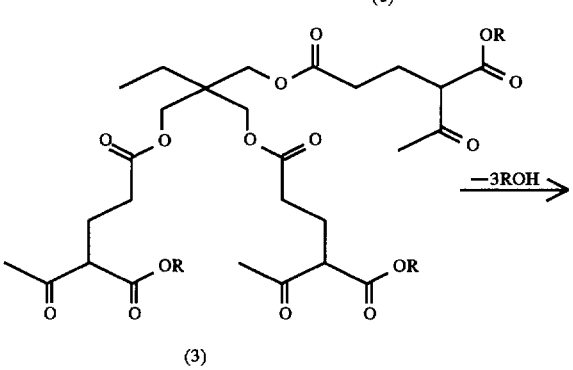

(3)

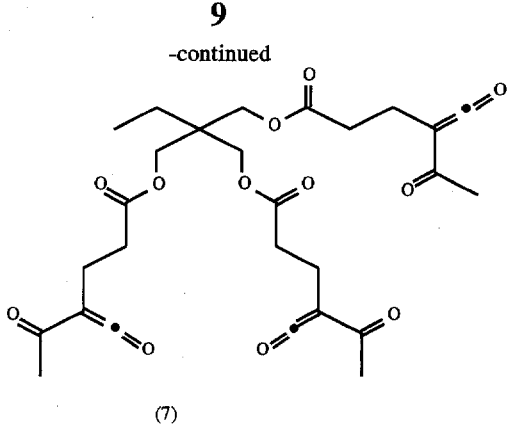

(7)

wherein R'=trimethylolpropane

As a further aspect of the present invention, there is provided a curable enamel composition further comprising one or more cross-linking catalysts, for example, dibutyl tin dilaurate; stearic acid; butyl stannoic acid; dibutyl tin oxide; zinc acetylacetonate; and 1,3-diacetoxy-1,1,3,3-tetrabutyldistannoxane.

As a further aspect of the present invention there is provided a cross-linkable enamel composition as described above, further comprising one or more leveling, rheology, and flow control agents such as silicones, fluorocarbons or cellulosics; flattening agents; pigment wetting and dispersing agents and surfactants; ultraviolet (UV) absorbers; UV light stabilizers; tinting pigments; defoaming and antifoaming agents; anti-settling, anti-sag and bodying agents; anti-skinning agents; anti-flooding and anti-floating agents; fungicides and mildewicides; corrosion inhibitors; thickening agents; or coalescing agents.

Specific examples of such additives can be found in *Raw Materials Index*, published by the National Paint & Coatings Association, 1500 Rhode Island Avenue, N.W., Washington, D.C. 20005.

Examples of flattening agents include synthetic silica, available from the Davison Chemical Division of W. R. Grace & Company under the tradename SYLOID®; polypropylene, available from Hercules Inc., under the tradename Hercoflat®; synthetic silicate, available from J. M. Huber Corporation under the tradename ZEOLEX®.

Examples of dispersing agents and surfactants include sodium bis(tridecyl)sulfosuccinnate, di(2-ethyl hexyl) sodium sulfosuccinnate, sodium dihexylsulfosuccinnate, sodium dicyclohexyl sulfosuccinnate, diamyl sodium sulfosuccinnate, sodium diisobutyl sulfosuccinnate, disodium iso-decyl sulfosuccinnate, disodium ethoxylated alcohol half ester of sulfosuccinnic acid, disodium alkyl amido polyethoxy sulfosuccinnate, tetrasodium N-(1,2-dicarboxyethyl)-N-oxtadecyl sulfosuccinnamate, disodium N-octasulfosuccinnamate, sulfated ethoxylated nonylphenol, 2-amino-2-methyl-1-propanol, and the like.

Examples of viscosity, suspension, and flow control agents include polyaminoamide phosphate, high molecular weight carboxylic acid salts of polyamine amides, and alkylene amine salts of an unsaturated fatty acid, all available from BYK Chemie U.S.A. under the tradename ANTI TERRA®. Further examples include polysiloxane copolymers, polyacrylate solution, cellulose esters, hydroxyethyl cellulose, hydrophobically-modified hydroxyethyl cellulose, hydroxypropyl cellulose, polyamide wax, polyolefin wax, carboxymethyl cellulose, ammonium polyacrylate, sodium polyacrylate, and polyethylene oxide.

Several proprietary antifoaming agents are commercially available,for example, under the tradename BRUBREAK of Buckman Laboratories Inc., under the BYK® tradename of BYK Chemie, U.S.A., under the Foamaster® and NOPCO® tradenames of Henkel Corp./Coating Chemicals, under the DREWPLUS® tradename of the Drew Industrial Division of Ashland Chemical Company, under the TROYSOL® and TROYKYD® tradenames of Troy Chemical Corporation, and under the SAG® tradename of Union Carbide Corporation.

Examples of fungicides, mildewcides, and biocides include 4,4-dimethyloxazolidine, 3,4,4-trimethyloxazolidine, modified barium metaborate, potassium N-hydroxy-methyl-N-methyldithiocarbamate, 2-(thiocyanomethylthio)benzothiazole, potassium dimethyl dithiocarbamate, adamantane, N-(trichloromethylthio) phthalimide, 2,4,5,6-tetrachloroisophthalonitrile, orthophenyl phenol, 2,4,5-trichlorophenol, dehydroacetic acid, copper naphthenate, copper octoate, organic arsenic, tributyl tin oxide, zinc naphthenate, and copper 8-quinolinate.

Examples of U.V. absorbers and U.V. light stabilizers include substituted benzophenone, substituted benzotriazoles, hindered amines, and hindered benzoates, available from American Cyanamide Company under the tradename CYAZORB UV, and diethyl-3-acetyl-4-hydroxybenzyl-phosphonate, 4-dodecyloxy-2-hydroxy benzophenone, and resorcinol monobenzoate.

Such paint or coating additives as described above form a relatively minor proportion of the enamel composition, preferably about 0.05 weight % to about 5.00 weight %.

As a further aspect of the present invention, there is provided a curable enamel composition as set forth above, further comprising one or more pigments in a concentration of about 1 to about 70 weight percent, preferably about 30 to about 60 weight percent, based on the total weight of components (a) and (b) of the composition.

Pigments suitable for use in the enamel compositions envisioned by the present invention are the typical organic and inorganic pigments, well-known to one of ordinary skill in the art of surface coatings, especially those set forth by the *Colour Index*, 3d Ed., 2d Rev., 1982, published by the Society of Dyers and Colourists in association with the American Association of Textile Chemists and Colorists. Examples include, but are not limited to the following: CI Pigment White 6 (titanium dioxide); CI Pigment Red 101 (red iron oxide); CI Pigment Yellow 42, CI Pigment Blue 15, 15:1, 15:2, 15:3, 15:4 (copper phthalocyanines); CI Pigment Red 49:1; and CI Pigment Red 57:1.

Upon formulation above, the curable enamel compositions is then applied to the desired substrate or article, e.g., steel, aluminum, or galvanized sheeting (either primed or unprimed), heated (i.e., cured) to a temperature of about 140° C. to about 275° C., for a time period of 1–120 minutes and subsequently allowed to cool. Thus, as a further aspect of the present invention, there is provided a shaped or formed article which has been coated with the thermosetting coating compositions of the present invention and cured.

Further examples of typical application and curing methods can be found in U.S. Pat. Nos. 4,737,551 and 4,698,391, incorporated herein by reference.

As a further aspect of the present invention, there is provided a coating which results from the application and curing of the curable enamel composition as set forth above.

Experimental Section

General $^1$H and $^{13}$C NMR spectra were obtained on a Varian Model Gemini 300 in $CDCl_3$ at frequencies of 300 and 75 MHZ respectively.

The applicable test procedures are as follows:
1. Testing Coated Metal Specimens at 100 Percent Relative Humidity—Cleveland Humidity Test (ASTM Method D 2247)
2. Film Thickness (General Electric Gage, Type B)
3. Film Hardness (Pencil Method, ASTM 3363-74, Reapproved 1980)
4. Solvent Resistance (methyl ethyl ketone (MEK) dynamic rub test, ASTM Method D 1308)
5. Impact Resistance (ASTM Method D 2794-84)
6. Resin molecular weight—GPC
7. OH Value determined by titration and are in units of mg KOH consumed per gram of polymer.
8. Acid Number (ASTM Method D 465). The units of this value are the same as the OH value.

The following resins were used in the evaluations:

RESIN A: This material was an acrylic resin prepared from 20 mol % hydroxyethyl methacrylate and 80 mol % methyl methacrylate and had a hydroxyl value of 106. The resin was used as a 60% solids solution in EEP.

RESIN B: This material was a polyester prepared using a two-stage addition procedure from 2.47 moles neopentyl glycol, 0.78 moles trimethylolpropane, 1.73 moles 1,4-cyclohexanedicarboxylic acid, and 1.17 moles phthalic anhydride. The material had a Mw=12160, a Mn=4300, a hydroxyl value of 104, and an acid value of 9. This material was thinned with xylene and used as a 75% solids solution.

RESIN C: Same as Resin B except a hydroxyl value of 103, an acid value of 4.5, a Mw=23082, and a Mn=2692. This material was thinned with xylene and used as a 75% solids solution.

RESIN D: This material was a polyester prepared using a two-staged addition procedure from 2.30 moles neopentyl glycol, 0.86 moles trimethylolpropane, 1.44 moles isophthalic acid, and 1.44 moles adipic acid. The material had a Mn=2573, a hydroxyl value of 88, and an acid value of 3. This material was used as a 99.2% solids formulation.

EXAMPLE 1

Preparation of Pentanedioic acid, 2-acetyl-, 5,5'-[2-[[[4-[(1,1-dimethylethoxy)carbonyl]-1,5-dioxohexyl]oxy]methyl]-2-ethyl-1,3-propanediyl]1,1'-bis (1,1-dimethylethyl)ester, 3

In a 3 L, single-neck flask equipped with a nitrogen inlet and a magnetic stir bar was introduced 498 mL of tert-butyl acetoacetate (3.0 mol) and 148.2 g of trimethylolpropane triacrylate (0.50 mol) to 1.5 L of toluene at 23° C. To this well-stirred solution was added 8.64 g of tetramethylguanidine (75 mmol) over 8 minutes. After 2 hours, the mixture was concentrated under reduced pressure at 50°–55° C. The residue was diluted with an equal volume of 50% ethyl acetate in heptane then filtered through a small plug of silica gel. An additional 500 mL of 50% ethyl acetate in heptane was filtered through the silica gel and the combined filtrates concentrated under reduced pressure. The residue was distilled at 40° C. (0.8 mm of Hg) to remove the excess tert-butyl acetoacetate. The pot residue was then flash chromatographed through silica gel using 15%, 20%, 30%, then 50% ethyl acetate in heptane. The fractions which contained the desired product, 3, were concentrated under reduced pressure. FDMS: 770.

$^1$H NMR: δ 3.99 (s, 6H); 3.41 (t, J=7.3 Hz, 3H); 2.34 (m, 6H); 2.22 (s, 9H); 2.08 (m, 6H); 1.45 (s, 27H, tBu CH$_3$); 1.43–1.47 (m, 2H); 0.86 (t, J=7 Hz, 3H).

$^{13}$C NMR: δ 203.2, 172.8, 168.9, 82.8, 64.3, 59.9, 41.3, 31.9, 29.6, 28.4, 23.3, 7.9.

EXAMPLE 2

Preparation of Pentanedioic acid, 2-acetyl-, 5,5'-[2-[[[4-[(1,1-dimethylethoxy)carbonyl]- 1,5-dioxohexyl]oxy]methyl]-2-ethyl-1,3-propanediyl]1,1'-bis(1,1-dimethylethyl)ester, 3

This material was prepared as in Example 1 except using 498 mL of tert-butyl acetoacetate (3.0 mol), 29.63 g of trimethylolpropane triacrylate (0.10 mol), and 1.73 g of tetramethylguanidine (15 mmol) in 300 mL of toluene. Total isolated product after chromatography was 35.43 g (46%).

EXAMPLE 3

Preparation of Pentanedioic acid, 2-acetyl-, 5,5'-[2-[[[4-[(1,1-dimethylethoxy)carbonyl]-1,5-dioxohexyl]oxy]methyl]-2-ethyl-1,3-propanediyl]1,1'-bis(1,1-dimethylethyl)ester, 3

This material was prepared as in Example 1 except using 23.73 g of tert-butyl acetoacetate (150 mmol), 14.82 g of trimethylolpropane triacrylate (50 mmol), and 1.63 g of a 25% solution of sodium methoxide in methanol (7.5 mmol) in place of tetramethylguanidine in 125 mL of toluene at 50° C.

EXAMPLE 4

Preparation of Pentanedioic acid, 2-acetyl-, 5,5'-[2-[[[4-[(1,1-dimethylethoxy)carbonyl]-1,5-dioxohexyl]oxy]methyl]-2-ethyl-1,3-propanediyl]1,1'-bis(1,1-dimethylethyl)ester, 3

This material was prepared as in Example 3 except no purification by column chromatography was done. The reaction mixture was only filtered through a small plug of silica gel to remove the sodium methoxide. The reaction mixture was then concentrated under reduced pressure at 50°–55° C. and the residue used as is in future formulations.

EXAMPLE 5

Preparation of Pentanedioic acid, 2-acetyl-, 5,5'-[2-[[[4-[(1,1-dimethylethoxy)carbonyl]-1,5-dioxohexyl]oxy]methyl]-2-ethyl-1,3-propanediyl]1,1'-bis(1,1-dimethylethyl)ester, 3

This material was prepared as in Example 1 except 189.8 g of tert-butyl acetoacetate (1.2 mol), 59.26 g of trimethylolpropane triacrylate (0.20 mol) and 3.46 g of tetramethylguanidine (30 mmol) were reacted in 600 mL of toluene at 50° C. for 4 hours. Purification by column chromatography used 10% then 20% ethyl acetate in heptane.

EXAMPLES 6 AND COMPARATIVE EXAMPLE 1

Formulations were prepared from compound 3 (prepared as in Example 2) and acrylic resin A as follows:

| Example # | 6 | C-1 |
| --- | --- | --- |
| Compound 3 | 24.5 g | — |
| Resin A (as 60% solids) | 84.3 g | 125 g |

| Example # | 6 | C-1 |
|---|---|---|
| TiO₂ R900 | 72.5 g | 83.3 g |
| Solvent | 90 mL | 90 mL |
| Flow Control | 0.25 g | 0.25 g |

Solvent = 50:30:20 MEK/EEP/MAK
Flow Control = FC-430 as 20% solution in iPrOH

Coatings of various thicknesses were prepared on phosphated steel panels using a wet film applicator and cured at 150°–200° C. The properties of the resulting formulations are given in Table 1. The improved MEK rub resistance data for Example 6 relative to Comparative Example 1 indicate that material 3 is crosslinking acrylic polymer A.

EXAMPLES 7 AND COMPARATIVE EXAMPLE 2

Formulations were prepared from compound 3 (prepared as in Example 3) and polyester resin B as follows:

| Example # | 7 | C-2 |
|---|---|---|
| Compound 3 | 11.3 g | — |
| Resin B (as 75% solids) | 31.6 g | 46.7 g |
| TiO₂ R900 | 28.6 g | 31.1 g |
| Solvent | 20 mL | 20 mL |
| Flow Control | 0.10 g | 0.10 g |

Solvent = 50:30:20 MEK/EEP/MAK
Flow Control = FC-430 as 20% solution in iPrOH

Coatings of various thicknesses were prepared on phosphated steel panels using a wet film applicator and cured at 150°–200° C. The properties of the resulting formulations are given in Table 2. The improved MEK rub resistance data for Example 7 relative to Comparative Example 2 indicate that material 3 is crosslinking polyester polymer B.

EXAMPLES 8 AND COMPARATIVE EXAMPLE 2

Formulations were prepared from compound 3 (prepared as in Example 4) and polyester resin B as follows:

| Example # | C-2 | 8 |
|---|---|---|
| Compound 3 | — | 11.3 g |
| Resin B as 75% solids) | 46.7 g | 31.6 g |
| TiO₂ R900 | 31.1 g | 28.6 g |
| Solvent | 20 mL | 20 mL |
| Flow Control | 0.10 g | 0.17 g |

Solvent = 50:30:20 MEK/EEP/MAK
Flow Control = FC-430 as 20% solution in iPrOH

Coatings of various thicknesses were prepared on phosphated steel panels using a wet film applicator and cured at 150°–180° C. The properties of the resulting formulations are given in Table 3. The improved MEK rub resistance data for Example 8 relative to Comparative Example 2 indicate that material 3 is crosslinking polyester polymer B.

EXAMPLES 9–11

Formulations were prepared from compound 3 (prepared as in Example 3), Cymel 303 (a hexamethyl methoxymelamine crosslinker), and polyester resin B or C as follows:

| Example # | 9 | 10 | 11 |
|---|---|---|---|
| Compound 3 | 7.58 g | 3.50 g | 5.26 g |
| Cymel 303 | 3.79 g | 7.00 g | 5.26 g |
| Resin B (as 75% solids) | 35.39 g | 32.67 g | — |
| Resin C (as 75% solids) | — | — | 32.68 g |
| TiO₂ R900 | 31.17 g | 28.78 g | 28.80 g |
| Solvent | 22 mL | 20 mL | 20 mL |
| Flow Control | 0.19 g | 0.18 g | 0.18 g |
| p-Toluenesulfonic acid | 0.19 g | 0.18 g | 0.18 g |

Solvent = 50:30:20 MEK/EEP/MAK
Flow Control = FC-430 as 20% soli%tion in iPrOH
p-Toluenesulfonic acid = 40% solution in iPrOH Coatings of various thicknesses were prepared on phosphated steel panels using a wet film applicator and cured at 150°–180° C. The properties of the resulting formulations are given in Table 4. The improved MEK rub resistance data for Examples 9, 10, and 11 relative to Comparative Example 2 indicate that the combination of compound 3 and Cymel 303 is crosslinking polyester resins B and C.

EXAMPLES 7, 12 AND COMPARATIVE EXAMPLES 3 AND 4

Formulations were prepared from compound 3 or Cymel 303 and either resin B or D as follows:

| Example | 7 | 12 | C-3 | C-4 |
|---|---|---|---|---|
| Compound 3 | 11.3 g | 5.75 g | — | — |
| Cymel 303 | — | — | 8.75 g | 8.75 g |
| Resin B | 31.6 g | — | 35 g | 35 g |
| Resin D | — | 14.46 g | — | — |
| TiO2 R900 | 28.6 g | 13.43 g | 29.2 g | 29.2 g |
| Solvent | 20 mL | 12 mL | 20 mL | 20 mL |
| Flow Control | 0.10 g | 0.08 g | 0.17 g | 0.17 g |
| p-TSA | — | — | 0.13 g | 0.22 g |

Solvent = 50:30:20 MEK/EEP/MAK
Flow Control = PC-430 as 20% solution in iPrOH
p-TSA = p-Toluenesulfonic acid as 40% solution in iPrOH Coatings of various thicknesses were prepared on phosphated steel panels using a wet film applicator and cured at 150°–180° C. The properties of the resulting formulations are given in Table 5. The improved MEK rub resistance data for Examples 7, 12, C-3, and C-4 relative to Comparative Example 2 indicate that both compound 3 and Cymel 303 is crosslinking with polyester resins B and D. Further examination of this data suggests that the acetylglutarate ester crosslinkers of the present invention when compared to the hexamethyl methoxymelamine control provide coatings with comparable solvent resistance, pencil hardness, and impact strength.

TABLE 1

| Example # | Cure[a] Conditions | Thickness (mils) | MEK RUB |
|---|---|---|---|
| 6 | 150/30 | 1.12 | 200+ |
| 6 | 160/30 | 1.19 | 250+ |
| 6 | 180/30 | 0.96 | 500 |
| 6 | 200/30 | 1.17 | 500 |
| C-1 | 150/30 | 1.07 | 200 |
| C-1 | 160/30 | 1.19 | 250 |

TABLE 1-continued

| Example # | Cure[a] Conditions | Thickness (mils) | MEK RUB |
|---|---|---|---|
| C-1 | 180/30 | 0.94 | 200 |
| C-1 | 200/30 | 1.05 | 200 |

[a]Temperature (°C.) and time (min) respectively.

TABLE 2

| Example # | Cure[a] Conditions | Thickness (mils) | MEK RUB | Impact (F/R) | Pencil Hardness |
|---|---|---|---|---|---|
| 7 | 150/30 | 1.48 | 150 | 160/160 | F |
| 7 | 160/30 | 1.71 | 400 | 160/160 | 2H |
| 7[b] | 170/30 | 1.47 | 450 | 160/160 | 4H |
| 7[b] | 180/30 | 1.61 | 500 | 160/160 | 4H |
| 7 | 200/30 | 1.47 | 500 | — | 4H |
| C-2 | 150/30 | — | <4 | — | — |
| C-2 | 160/30 | — | <4 | — | — |
| C-2 | 170/30 | 1.35 | <4 | — | — |
| C-2 | 180/30 | 1.45 | <4 | — | — |
| C-2 | 200/30 | 1.38 | <4 | — | — |

[a]Temperature (°C.) and time (min) respectively
[b]exposure to Cleveland Humidity conditions showed no signs of blistering or coating degradation after 1000 hours.

TABLE 3

| Example # | Cure[a] Conditions | Thickness (mils) | MEK RUB | Pencil Hardness |
|---|---|---|---|---|
| C-2 | 150/30 | — | <4 | — |
| C-2 | 160/30 | — | <4 | — |
| C-2 | 170/30 | 1.35 | <4 | — |
| C-2 | 180/30 | 1.45 | <4 | — |
| 8 | 150/30 | 1.53 | 30 | F |
| 8 | 160/30 | 1.64 | 100 | H |
| 8 | 170/30 | 1.72 | 150 | 2H/3H |
| 8 | 180/30 | 1.76 | 100 | 2H/3H |

[a]Temperature (°C.) and time (min) respectively.

TABLE 4

| Example # | Cure[a] Conditions | Thickness (mils) | MEK RUB | Pencil Hardness | Impact (F/R) |
|---|---|---|---|---|---|
| 9 | 150/30 | 2.39 | 300 | 2B | 160/140 |
| 9 | 160/30 | 2.51 | 500+ | F | 160/160 |
| 9 | 170/30 | 2.35 | 500+ | H | 160/160 |
| 9 | 180/30 | 2.43 | 500+ | H | 160/160 |
| 10 | 150/30 | 2.54 | 500+ | 2B | 160/140 |
| 10 | 160/30 | 2.30 | 500+ | F | 160/160 |
| 10 | 170/30 | 2.09 | 500+ | H | 160/160 |
| 10 | 180/30 | 2.44 | 500+ | H | 160/160 |
| 11 | 150/30 | 2.07 | 400 | B | 160/140 |
| 11 | 160/30 | 2.14 | 500+ | H | 160/160 |
| 11 | 170/30 | 2.36 | 500+ | H | 160/160 |
| 11 | 180/30 | 2.14 | 500+ | H | 160/160 |

[a]Temperature (°C.) and time (min) respectively.

TABLE 5

| Example # | Cure[a] Conditions | Thickness (mils) | MEK RUB | Pencil Hardness | Impact (F/R) |
|---|---|---|---|---|---|
| 7 | 150/30 | 1.48 | 150 | F | 160/160 |
| 7 | 160/30 | 1.71 | 400 | 2H | 160/160 |
| 7 | 170/30 | 1.47 | 450 | 4H | 160/160 |
| 7 | 180/30 | 1.61 | 500+ | 4H | 160/160 |
| 1 | 150/30 | 1.84 | 135 | B | 160/160 |
| 12 | 160/30 | 1.92 | 400 | F | 160/160 |
| 12 | 170/30 | 2.15 | 300 | F | 160/160 |
| 12 | 180/30 | 2.31 | 500+ | F | 160/160 |
| C-3 | 150/30 | — | 150 | F | 60/<20 |
| C-3 | 160/30 | — | 100 | F | 40/<20 |
| C-3 | 170/30 | — | 400 | 4H | 160/160 |
| C-3 | 180/30 | — | 400+ | 2H/3H | 160/160 |
| C-4 | 150/30 | — | 200 | H | 60/40 |
| C-4 | 160/30 | 1.82 | 250 | H | 160/160 |
| C-4 | 170/30 | — | 500+ | 3H | 160/160 |
| C-4 | 180/30 | 1.78 | 500+ | 4H | 160/160 |

[a]Temperature (°C.) and time (min) respectively.

We claim:

1. A thermosetting coating composition comprising
   (I) about 15 to 80 weight percent of a curable polymer;
   (II) about 0 to 50 weight percent of a solvent; and
   (III) about 10 to about 40 weight percent of a crosslinking compound selected from the group consisting of

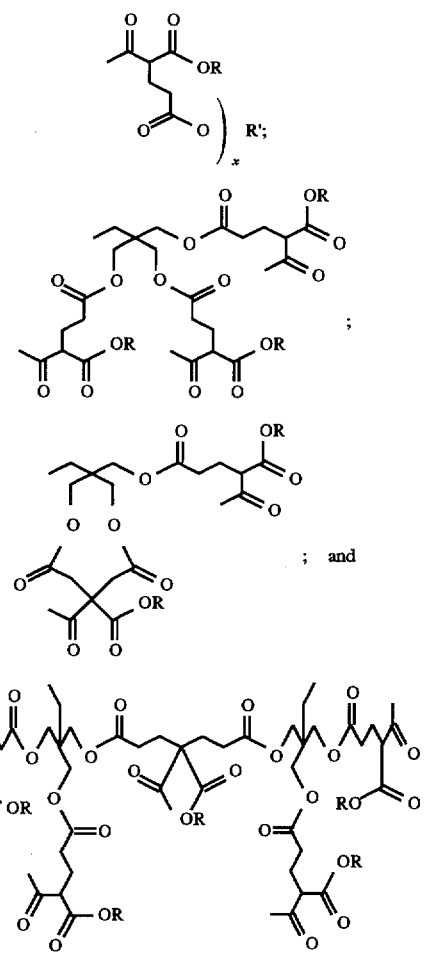

wherein R is t-butyl, t-amyl, or phenyl, and R' is a di- or trifunctional polyol, and x is an integer of from 2 to 5.

2. The composition of claim 1, wherein component (III) is

3. The composition of claim 1, wherein component (III) is

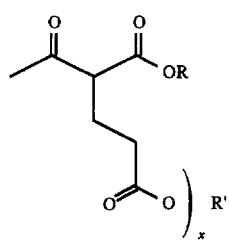

4. The composition of claim 1, wherein component (III) is

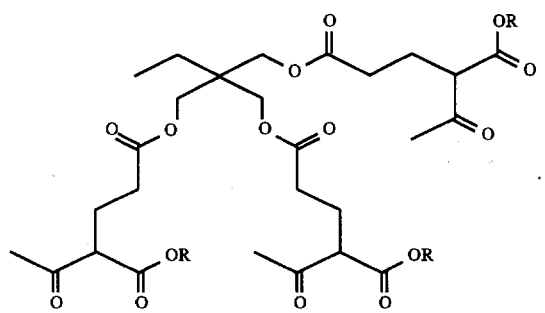

5. The composition of claim 1, wherein component (III) is

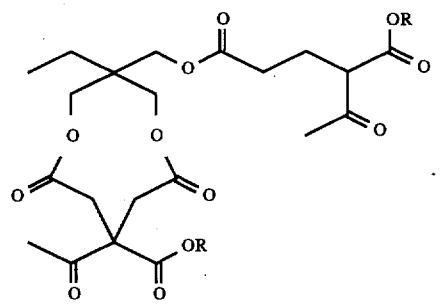

6. The composition of claim 1, further comprising one or more pigments.

7. The composition of claim 1, further comprising one or more leveling, rheology, and flow control agents; flatting agents; pigment wetting and dispersing agents and surfactants; ultraviolet absorbers; ultraviolet light stabilizers; tinting pigments; defoaming and anti-foaming agents; anti-settling, anti-sag and bodying agents; anti-skinning agents; anti-flooding and anti-floating agents; fungicides and mildewcides; corrosion inhibitors; thickening agents; or coalescing agents.

8. The composition of claim 1, further comprising a melamine-type crosslinking compound.

9. A shaped or formed article coated with the cured thermosetting coating composition of claim 1.

10. The composition of claim 1, wherein component III has the structure

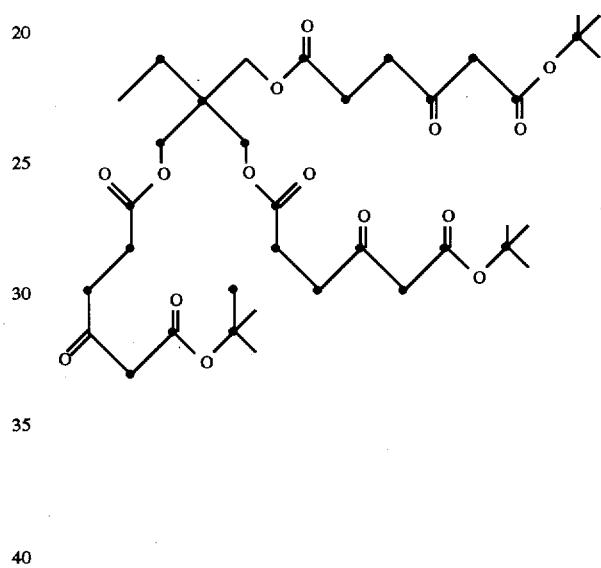

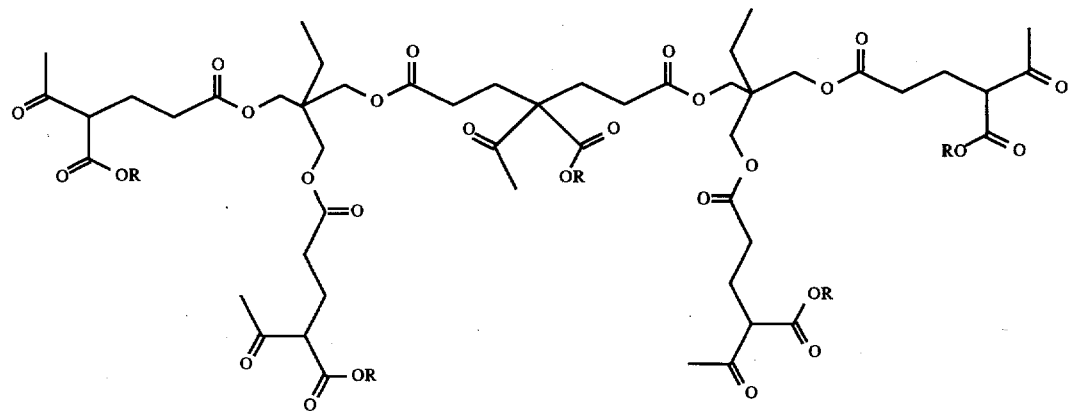

* * * * *